United States Patent [19]
White et al.

[11] Patent Number: 5,876,609
[45] Date of Patent: Mar. 2, 1999

[54] PROCESS FOR TREATING METHYLCHLOROSILANES BY-PRODUCTS

[75] Inventors: Michael Lee White, Attleboro, Mass.; Sunita Singh Baghel, Rensselaer, N.Y.; Luisito Alvarez Tolentino, Clifton Park, N.Y.; Mark Kromer Barr, Ballston Lake, N.Y.; David Cheney DeMoulpied, Clifton Park, N.Y.; William Lee Gately, Burnt Hills, N.Y.; Jan-Willem Goedmakers; Jeffrey David Hallen, both of Clifton Park, N.Y.; Edward Francis Kennedy, Waterford, N.Y.; Bang Mo Kim, Scotia, N.Y.; Ray Walton Shade; Matthew David Butts, both of Clifton Park, N.Y.

[73] Assignee: General Electric Company, Schenectady, N.Y.

[21] Appl. No.: 827,554

[22] Filed: Mar. 28, 1997

[51] Int. Cl.⁶ .................................. C02F 1/54; C02F 1/62
[52] U.S. Cl. ......................... 210/725; 210/727; 210/728; 210/732; 210/912; 556/472
[58] Field of Search .................................. 210/724, 725, 210/727, 728, 729, 732, 912; 556/472

[56] References Cited

U.S. PATENT DOCUMENTS

| | | |
|---|---|---|
| 2,380,995 | 8/1945 | Rochow . |
| 4,221,691 | 9/1980 | Danielson et al. . |
| 4,393,229 | 7/1983 | Ritzer et al. . |
| 4,408,030 | 10/1983 | Marko . |
| 4,690,810 | 9/1987 | Breneman et al. . |
| 4,758,352 | 7/1988 | Feldner et al. ............................ 210/719 |
| 4,960,523 | 10/1990 | Degen et al. . |
| 5,169,970 | 12/1992 | Ohkawa ................................... 556/459 |
| 5,175,329 | 12/1992 | Bokerman et al. . |
| 5,246,682 | 9/1993 | Ruff et al. . |
| 5,288,892 | 2/1994 | Pachaly et al. . |
| 5,342,430 | 8/1994 | Grocela-Kathe et al. ................ 75/746 |
| 5,374,310 | 12/1994 | Bunce et al. . |
| 5,430,168 | 7/1995 | Ferguson et al. . |
| 5,651,807 | 7/1997 | Gundersen et al. .................... 75/10.48 |
| 5,651,895 | 7/1997 | Gordon ................................... 210/912 |

FOREIGN PATENT DOCUMENTS 3523541  7/1985  Germany .

OTHER PUBLICATIONS

G Laroze and L Gilbert, Silicon for the Chemical Industry III, "New Catalytic Process for the Cleavage of Disilanes".

*Primary Examiner*—Jay H. Woo
*Assistant Examiner*—Betsey J. Morrison
*Attorney, Agent, or Firm*—Noreen C. Johnson; Douglas E. Stoner

[57] ABSTRACT

The instant invention relates to a novel process for the hydrolysis of the by-products produced during the manufacture of methyldichlorosilanes comprising combining the by-products with an aqueous medium, optionally comprising a surfactant, at a pH range of at least about 7 and at a temperature of above about 0° C. to produce a solid material in which copper and other metals are retained in a solid phase thereby resulting in a product with a high copper content.

11 Claims, No Drawings

PROCESS FOR TREATING METHYLCHLOROSILANES BY-PRODUCTS

FIELD OF THE INVENTION

The instant invention relates to a novel process for the hydrolysis of selected by-products resulting from the manufacture of methyl chlorosilanes.

BACKGROUND OF THE INVENTION

The present invention relates to the hydrolysis of by-products generated during the manufacture of methyl chlorosilanes. The basic process for the manufacture of such silane compounds is well known and is described in U.S. Pat. No. 2,380,995. Such a process generates by-products which at the present time have little or no commercial value. These by-products can present serious problems in their safe and environmentally acceptable ultimate disposal. The by-product streams of immediate interest are those consisting of high-boiling liquids (>75° C.); suspended silicon powder; elevated levels of copper, zinc and tin; as well as, a variety of other metals. Upon uncontrolled exposure to moisture and air, these materials may be easily ignited and/or form strong acid mists and liquid streams.

Procedures for the disposal of these by-products, and similar ones, are reported in U.S. Pat. Nos. 4,221,691; 4,408,030; 4,758,352; and 4,960,523; and in German patent DE3523541A1.

U.S. Pat. No. 4,221,691 discloses a method of hydrolyzing polyfunctional chlorosilicon compositions which involves adding a hydrocarbon oil to the chlorosilicon composition, prior to hydrolysis in an aqueous medium containing concentrated HCl and/or $CaCl_2$. Hydrolysis of the comparable streams from the methylchlorosilane process is also disclosed in U.S. Pat. No. 4,408,030. This process utilizes concentrated HCl to hydrolyze the waste stream containing silicon chlorides. The other patents disclose similar processes but do not address the disposition of copper present in the original by-product stream.

There is thus a need to develop a process that can hydrolyze the methylchlorosilane by-products to produce a solid material containing the copper and other metals. Among other benefits, such a product has value as a source of copper for recovery. This process has the additional advantage of minimizing the concentration of heavy metals in the resultant liquid stream thereby reducing any waste treatment problems.

An effective hydrolysis process should produce a final passivated solid that has a high flash point, little or no gas evolution, non-sticky, free-flowing and non-dusting material that can be readily handled and transported.

SUMMARY OF THE INVENTION

The instant invention comprises a process for treating by-products generated during the production of methylchlorosilanes to yield at least two separable phases, the process comprising hydrolyzing the by-products combining the products with an aqueous medium, the aqueous medium optionally comprising a surfactant, at a pH of about 7 and above, and at a temperature above about 0° C. The solids in the resultant slurry are recovered by filtration, or other mechanical means and dried to a controlled moisture level.

DETAILED DESCRIPTION

The instant invention comprises a process for treating selected by-products generated during the production of methylchlorosilanes to yield at least two separable phases, the process comprising hydrolyzing the by-products combining the products with an aqueous medium, the aqueous medium optionally comprising a surfactant, at a pH of about 7 and above, and at a temperature of above about 0° C. The process yields at least two separable phases wherein the first phase comprises essentially inert solids, and the second phase comprises an aqueous solution, essentially free of metals, suitable for discarding in an industrial effluent stream with or without further treatment.

In a preferred embodiment the basic aqueous medium comprises a base selected from calcium hydroxide, calcium oxide, sodium oxide, sodium hydroxide, potassium oxide, potassium hydroxide, magnesium oxide, magnesium hydroxide, calcium carbonate, calcium bicarbonate, sodium carbonate, sodium bicarbonate, magnesium carbonate, and magnesium bicarbonate. Also provided by the present invention is an embodiment wherein the basic aqueous medium contains a surfactant selected from anionic or non-ionic surfactants such as alkyloxy(polyethyleneoxypropyleneoxy) isopropanol (commercially sold as Tergitol® which is produced and marketed by Union Carbide Corporation), polyoxyethylene(4)lauryl ether (commercially sold as Brij 30® by ICI), and a polyoxyethylene alkyl alcohol (sold as Renex KB® by ICI) and chemical equivalents thereof. Nonionic surfactants are preferred.

In another embodiment of the present invention is provided a process wherein the pH is maintained between about 7–12, the preferred pH range being 9–11. The process provided by the instant invention can be carried out at temperatures ranging from about 0° C. to at least about the boiling point of the aqueous medium, although a temperature range of 25°–95° C. is a typical range for the process provided by the instant invention. A preferred temperature range for the instant process being from about 35° C. to about 95° C.

In a further preferred embodiment, the aqueous medium comprises, at least in part, filter wash liquid and/or filtrate liquid, a base such as calcium hydroxide, a surfactant selected from anionic or non-ionic surfactants such as alkyloxy(polyethyleneoxypropyleneoxy)isopropanol (commercially sold as Tergitol® which is produced and marketed by Union Carbide Corporation), polyoxyethylene (4)lauryl ether (commercially sold as Brij 30® by ICI), and a polyoxyethylene alkyl alcohol (sold as Renex KB® by ICI) and chemical equivalents thereof. Nonionic surfactants are preferred. These surfactants generally are polyoxyethylene-polypropylene copolymers.

The compositions of the various by-product samples, generated during the manufacture of methylchlorosilanes, of the by-products utilized are summarized in Table 1. These compositions are considered typical for by-product streams, but considerable batch to batch variation can exist. For instance, the concentration of solids can vary up to about 60%, and the concentration of copper can vary up to about 25%. The liquid portion of samples may include numerous high boiling multi-functional alkylchlorosilanes, alkylchlorocarbosilanes, alkylchlorosiloxanes and alkylchlorooligosilanes, where the alkyl substituent is predominantly methyl, although others such as ethyl, propyl, may be present. Hydrocarbons and other species may also be present in varying concentrations, but usually at low levels. These by-products also contain metals that need to be removed.

TABLE 1

SAMPLE ANALYSIS

|        | Sample A | Sample B | Sample C |
|--------|----------|----------|----------|
| Solids | 39%      | 40%      | 40%      |
| Al     | 1.8%     | 0.98%    | 1.6%     |
| Fe     | 1.6%     | 1.3%     | ND       |
| Zn     | 1.3%     | 0.75%    | 1.1%     |
| Cu     | 10.0%    | 8.3%     | 7.7%     |
| Cl     | 26%      | 25%      | 32%      |

ND = Not determined

Although many compounds were identified by GC/MS in the liquid portion of the by-product samples, the primary species were oligosilanes, siloxanes, and carbosilanes, generally comprising three or more chlorine atoms, thus leading to a highly cross linked hydrolyzed structure.

The novel process of the instant invention was carried out at various temperatures. The temperature can be controlled by heating, cooling, by the rate of sample addition, or other techniques known to one skilled in the art. The reaction mixture of the instant novel process was agitated at different rates and the instant process utilized a sample to water ratio of from about 1:1 to about 1:20. All the reactions were carried out in closed systems which enabled measurement of the volume of hydrogen evolved.

The consolidated results for examples 1–4 are displayed in Table 2. The copper concentration of the solid product was determined by inductive coupling plasma following microwave digestion in $HF/HNO_3$. The amount of copper (Cu) and zinc (Zn) in the filtrate were determined by inductive coupling plasma. The chlorine (Cl) content in the solid was determined by Capillary Electrophoresis following microwave digestion in NaOH. The degree of "passivation" was determined by a volume displacement experiment, as described in the experimental section.

The following examples are provided to illustrate the present invention.

EXPERIMENTAL DETAILS

VOLUME DISPLACEMENT EXPERIMENTAL PROCEDURE 165 mL of 2.4% Tergitol® surfactant in water was preheated to about 90° C. in a 250 mL round bottom flask with a magnetic stir bar, by immersing in a constant temperature bath 5.0 g of the solid obtained as a product in examples 1–4 was ground with a mortar and pestle and then dumped into the flask and immediately fitted with a ground glass outlet connected to a Tygon™ tube leading to an inverted 100 mL burette filled with water. The rate and total volume of gas evolved were measured. The "passivation" results are expressed in mL of gas evolved after 45 minutes per g of dried sample. <6 mL/g is considered to be reasonably well "passivated." The composition of the gas evolved was determined to be primarily hydrogen ($H_2$), with less than 20% methane by GC/MS. <1% methane was observed for the samples with pH >7.

EXAMPLES

Example 1

2.01 kg of sample A was added in portions to a glass 25 L resin kettle fitted with an agitator blade containing 6 L of water and 446 g of CaO at about 22° C. Upon addition, the temperature increased to about 60+/−5° C. from the exotherm of the reaction and then was maintained at that temperature using an oil bath. A stirring rate of 350 RPM was utilized. After about two hours, the sample was vacuum filtered through medium grade filter paper and then washed with four 2 L aliquots of water. The sample was dried by exposure to the atmosphere for about 2 days. This sample was a granular solid which was completely "passivated" after drying.

Example 2

104.4 g of sample B was added to a glass jar fitted with high torque mixer, to which was added about 265 mL of water via an addition funnel. The temperature increased to 85+/−5° C. from the exotherm of the reaction and then was allowed to cool toward about 25° C. during the course of the reaction. After about twenty minutes, the sample was filtered through a medium grade paper filter on a funnel fitted with a vacuum line and then washed with three 100 mL aliquots of water. The resultant granular solid was then dried in a 30 torr vacuum oven at about 105° C. over night.

Example 3

48.5 g of Sample A was added to 300 g of an aqueous solution containing 16.3 g NaOH (this corresponds to 113% of the stoichiometric amount based on the chloride content) and a small amount of the Tergitol® surfactant. The temperature was maintained at about 80°–90° C. with a stirring rate of 1100 RPM. After about two hours the reaction mixture was vacuum filtered through a medium grade filter paper and then washed with two 100 g aliquots of water. The filter cake was dried under full vacuum at about 105° C. for about 15 hours.

Example 4

49.3 g of Sample A was added to 150 g of an aqueous solution containing 14.4 g NaOH (this corresponds to 99% of the stoichiometric amount based on the chloride content) and a small amount of the Tergitol® surfactant. The temperature was maintained at about 80°–90° C. with a stirring rate of about 1100 RPM. After about two hours the reaction mixture was vacuum filtered through a medium grade filter paper and recovered solids were dried at about 105° C. for about 15 hours.

TABLE 2

RESULTS AND ANALYSIS

| Ex. | Amount of Base Rel. to Chloride (% Stoichiometric) | Filtrate pH | Cu in Solids (%) | Chloride in Solids (%) | Cu in Filtrate (ppm) | Zn in Filtrate (ppm) | mL/g $H_2$ | Dry* Solids Yield (%) |
|---|---|---|---|---|---|---|---|---|
| 1 | 108  | ND  | 10.2 | 0.5 | 3   | 2    | 0   | 86 |
| 2 | 0    | <1  | 8.9  | 3.4 | 345 | 4176 | ND  | ND |
| 3 | 11.5 | 9.8 | ND   | 1.9 | <1  | <1   | 4.6 | ND |
| 4 | 100  | 4.4 | ND   | 2.7 | 38  | 3200 | 5.2 | ND |

ND: Not Determined
*Dry Solids yielded: (Weight Solids/Weight Initial) × 100

Example 5

To a 1 L resin kettle was added 16.5 g of $Ca(OH)_2$ followed by about 150 mL water. The mixture was heated to about 55° C. in an oil bath under high agitation (ca. 1100 rpm, maintained through out the experiment). After about 10 minutes 50 g of the mixture were added over 3 minutes by syringe. After about 2 hours at about 55°–60° C., the hot mixture was filtered on a Buchner funnel. The solid was then washed with hot water (ca. 95° C., 2×250 mL). The solid was dried in a vacuum oven for 14 hours at about 85° C. The solid was then analyzed for chloride content.

Example 6

The reaction conditions were essentially the same as in Example 5 except that the reaction was carried out in an aqueous solution of the Tergitol® surfactant (4.8% by weight), and the reaction temperature was maintained at about 65° C.

Example 7

Reaction conditions were about the same as in Example 5, except that (a) 13.8 g of $Ca(OH)_2$ were added, (b) the reaction temperature was maintained at about 92° C., and (c) the reaction time was extended to about 4 hours.

Example 8

Reaction conditions were about the same as in Example 7, except that the reaction was carried out in an aqueous solution of the Brig 30® surfactant (3% by weight).

Example 9

Reaction conditions were about the same as in Example 7 except that the reaction was carried out in an aqueous solution of the Renex® KB surfactant (3% by weight).

TABLE 3

EFFECT OF ADDED SURFACTANTS ON CHLORIDE CONTENT

| Example | Added Surfactant | % Cl in hydrolyzed solid |
|---|---|---|
| 5 | none       | 2.5  |
| 6 | Tergitol ® | 1.03 |
| 7 | none       | 1.5  |
| 8 | Brij ® 30  | 1.1  |
| 9 | Renex ® KB | 0.85 |

The above table illustrates the effect of surfactants on the amount of chloride in the hydrolyzed mixture. Thus Examples 5 and 7 which do not use any surfactant are left with a chloride content of 2.5% and 1.5% respectively after hydrolysis. Examples 6, 8, and 9 on the other hand contained a surfactant and the effect of the surfactant is seen by the decreased amount of chloride after hydrolysis, i.e., 0.85% to 1.1%.

As used herein, metals include zinc, aluminum, copper, tin, iron, and titanium. The term "essentially free" used herein indicates that the amount of metals present is less than about 550 ppm. Also, the term "inert solids" means the resulting solid, as discussed in the volume displacement experiment, which evolves less than 6 ml of hydrogen per gram of the resulting solid upon base hydrolysis. The resulting solids may also be referred to as passivated or inert solids.

What is claimed is:

1. A process for treatment of by-products generated during the production of methylchlorosilanes selected from the group consisting of high boiling liquids (>75° C.), and a mixture of high boiling liquids (>75° C.) and up to about 60% by weight of suspended silicon powder, the process comprising hydrolyzing the by-products by combining the products with an aqueous medium, the aqueous medium optionally comprising a surfactant, at a pH of from 9 to 11 and at a temperature above about 0° C.

2. A process of claim 1 wherein the process yields two separable phases wherein a first phase comprises essentially inert solids, and a second phase comprises an aqueous solution, essentially free of metals, suitable for discarding in an industrial effluent stream with or without further treatment.

3. A process of claim 2 wherein the aqueous medium comprises a base selected from an alkali metal oxide, alkali metal hydroxide, and alkali metal carbonate.

4. A process of claim 3 wherein the base is selected from calcium hydroxide, calcium oxide, sodium hydroxide, potassium hydroxide, and magnesium hydroxide.

5. A process of claim 4 wherein the base is selected from calcium hydroxide, calcium oxide, sodium hydroxide, and magnesium hydroxide.

6. A process of claim 5 wherein the base is calcium oxide or calcium hydroxide.

7. A process of claim 1 wherein the temperature ranges from about 0° C. to about 100° C.

8. A process of claim 7 wherein the temperature ranges from about 50° C. to about 95° C.

9. A process of claim 3 wherein the aqueous medium comprises a surfactant selected from alkylpolyetheralalcohol, polyethylenealkyloxy alcohol, and polyoxyethylene(4) lauryl ether.

10. A process of claim 9 wherein the surfactant is alkyloxy (polyethyleneoxypropyleneoxy)isopropanol.

11. A process of claim 3 comprising separating the solids using sedimentation, floatation, or centrifugation techniques, and isolating the aqueous medium for recovering salts, silicates, or for discharging to a waste water treatment facility.

* * * * *